: US 10,692,601 B2

(12) United States Patent
Tang et al.

(10) Patent No.: US 10,692,601 B2
(45) Date of Patent: Jun. 23, 2020

(54) CONTROLLING DEVICES BASED ON HIERARCHICAL DATA

(71) Applicant: HITACHI, LTD., Tokyo (JP)

(72) Inventors: Hsiu-Khuern Tang, San Jose, CA (US); Haiyan Wang, Fremont, CA (US); Hiroaki Ozaki, Mountain View, CA (US); Shuang Feng, Milpitas, CA (US); Abhay Mehta, Austin, TX (US)

(73) Assignee: HITACHI, LTD., Tokyo (JP)

( * ) Notice: Subject to any disclaimer, the term of this patent is extended or adjusted under 35 U.S.C. 154(b) by 973 days.

(21) Appl. No.: 15/246,685

(22) Filed: Aug. 25, 2016

(65) Prior Publication Data

US 2018/0060513 A1    Mar. 1, 2018

(51) Int. Cl.
*G06N 20/00*  (2019.01)
*G16H 40/63*  (2018.01)
*G16H 40/60*  (2018.01)
*G16H 40/20*  (2018.01)

(52) U.S. Cl.
CPC ............. *G16H 40/63* (2018.01); *G06N 20/00* (2019.01); *G16H 40/20* (2018.01); *G16H 40/60* (2018.01)

(58) Field of Classification Search
CPC ............ G06N 20/00; G06N 5/02; G06N 3/08; G06N 5/00
See application file for complete search history.

(56) References Cited

U.S. PATENT DOCUMENTS

2012/0072390 A1* 3/2012 Wang ....................... G06N 5/02
706/54

2018/0060513 A1* 3/2018 Tang ........................ G16H 40/63
2018/0109589 A1* 4/2018 Ozaki ..................... H04L 67/025

FOREIGN PATENT DOCUMENTS

WO    02/073532 A1    9/2002
WO    WO-02073532 A1 *  9/2002 ............... G06N 5/00

OTHER PUBLICATIONS

Vidhya, "A Complete Tutorial on Tree Based Modeling from Scratch (in R & Python)", website: https://www.analyticsvidhya.com/blog/2016/04/complete-tutorial-tree-based-modeling-scratch-in-python/, Apr. 12, 2016, pp. 1-28 (Year: 2016).*
Extended European Search Report received in corresponding European Application No. 17187788.9 dated Feb. 1, 2018.

* cited by examiner

*Primary Examiner* — Paulinho E Smith
(74) *Attorney, Agent, or Firm* — Mattingly & Malur, PC

(57) ABSTRACT

In some examples, a computing device may receive hierarchical data having a hierarchical structure including a plurality of levels. The computing device may determine a plurality of features based at least in part on the hierarchical data, and may select a subset of the features at a first level as candidates for consolidating to a next higher level in the hierarchical structure. The computing device may determine that a predicted loss of information from consolidating the subset of features is less than a threshold, and may revise the hierarchical structure to include a consolidated feature at the next higher level, rather than the subset of features. In some examples, a statistical model may be trained based on the revised hierarchical structure and used at least partially to make a determination, send a notification, and/or control a device.

19 Claims, 10 Drawing Sheets

200

| | 202 | 204 | 206 | |
|---|---|---|---|---|
| | LEVEL 1 | LEVEL 2 | LEVEL 3 | ... |
| | FLUIDS IN | IV FLUIDS | MORPHINE | |
| | FLUIDS IN | IV FLUIDS | SALINE | |
| | FLUIDS IN | BLOOD PRODUCTS | COMPONENT 1 | |
| | FLUIDS IN | BLOOD PRODUCTS | COMPONENT 2 | |
| | FLUIDS OUT | BLOOD | | |
| | FLUIDS OUT | URINE | | |
| | MEDICATIONS | DRUG 1 | | |
| | MEDICATIONS | DRUG 2 | | |
| | MEDICATIONS | IV FLUIDS | DRUG 1 | |
| | MEDICATIONS | IV FLUIDS | DRUG 3 | |
| | ASSESSMENTS | CONDITION 1 SEVERITY | | |
| | ASSESSMENTS | CONDITION 2 SEVERITY | | |
| | ⋮ | ⋮ | ⋮ | |

FIG. 2

| PATIENT ID | DATE | y | FEATURE 1 | FEATURE 2 | ... | FEATURE K | ... |
|---|---|---|---|---|---|---|---|
| 1 | 2016-05-01 | 1 | 500 | 30 | | ON | |
| 1 | 2016-05-02 | 1 | 250 | 30 | | ON | |
| 2 | 2016-05-01 | 0 | 100 | 0 | | ON | |
| 2 | 2016-05-02 | 1 | 50 | 26 | | OFF | |
| ... | ... | ... | ... | ... | | ... | |

FIG. 4

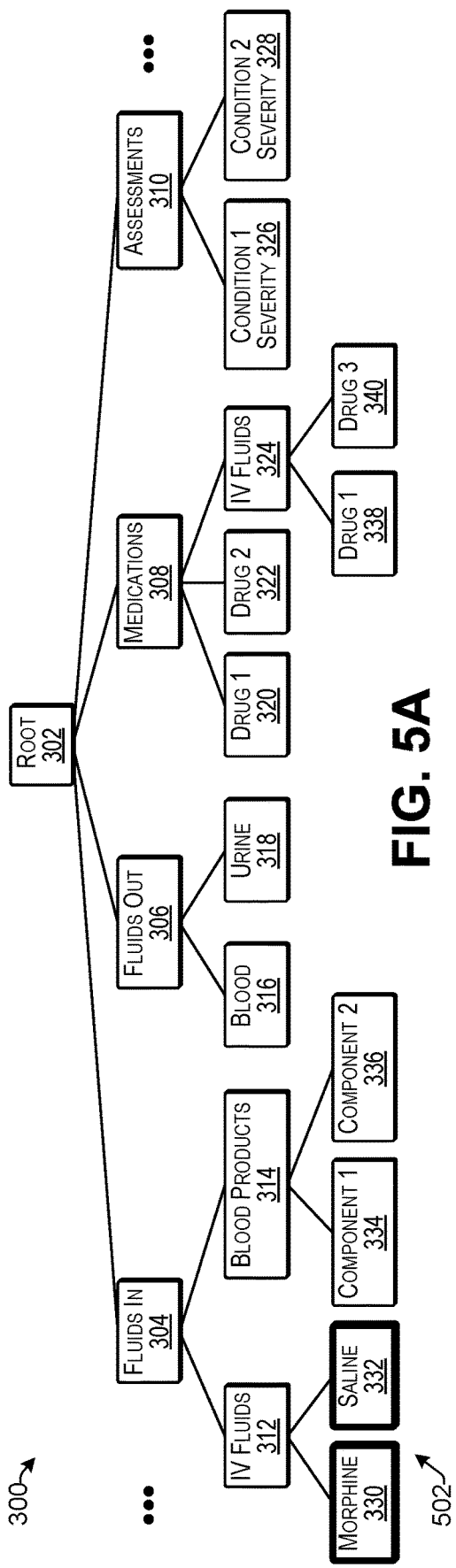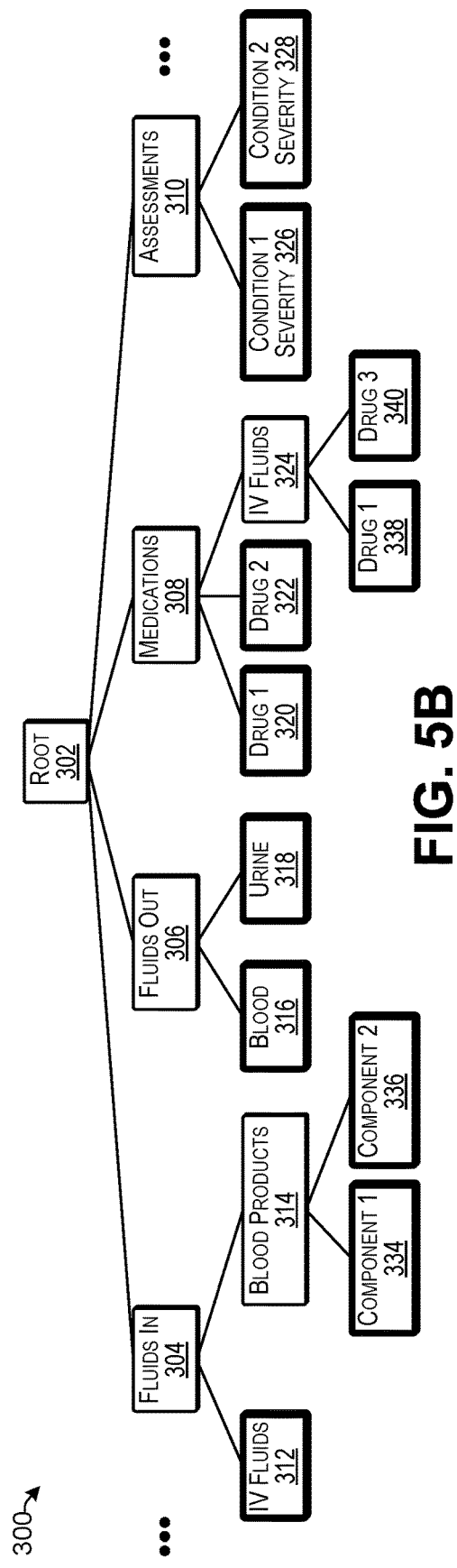

US 10,692,601 B2

CONTROLLING DEVICES BASED ON HIERARCHICAL DATA

BACKGROUND

Patients in hospitals and other medical care facilities frequently may be connected to, or otherwise monitored by, a plurality of different types of medical devices that monitor various bodily conditions. Each of these monitors may include one or more sensors and processing components that provide information about the patient. Additionally, patients may be treated by medical devices that provide treatment for one or more medical conditions. These devices also may provide sensor data indicative of their operation. Furthermore, caregivers, such as nurses, physicians, physician assistants, and other medical professionals may also record information about a patient as caregiver records. Examples of information that may be included in the caregiver records may include patient conditions, prognoses, treatment plans, prescriptions, types of medication, frequency of medication, tests performed, caregiver observations, and so forth.

Despite this tremendous amount of data, treatment of patients is often performed based on predetermined treatment regimens that may be manually managed by caregivers. For instance, caregivers may be responsible for manually turning on and off treatment devices and other medical devices. Additionally, caregiver judgment typically may be used for determining timing and frequency for applying treatment to a particular patient. However, caregivers may not be able to take into consideration all available data when determining timing of treatments, prognoses for a patient, long-term care plans, likelihood of readmission, or the like.

SUMMARY

Some implementations include arrangements and techniques for performing analysis, sending notifications, making determinations and/or controlling devices based on hierarchical data. As one example, a computing device may receive hierarchical data having a hierarchical structure including a plurality of hierarchical levels. The computing device may determine a plurality of model features based at least in part on the hierarchical data, and may select a subset of the features at a first level as candidates for consolidating to a next higher level in the hierarchical structure. The computing device may determine that a predicted loss of information from consolidating the subset of features is less than a threshold, and may revise the hierarchical structure to include a consolidated feature at the next higher level, rather than the subset of features. In some examples, a statistical model may be trained based on the revised hierarchical structure and used at least partially to make a determination, send a notification, and/or control a device.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 2 illustrates an example data structure including hierarchical data according to some implementations.

FIG. 4 illustrates an example data structure of a training data set for use with a statistical model according to some implementations.

FIGS. 5A-5B illustrate an example of the tree data structure in which features are consolidated into a higher level node according to some implementations.

DETAILED DESCRIPTION

Figure 1:
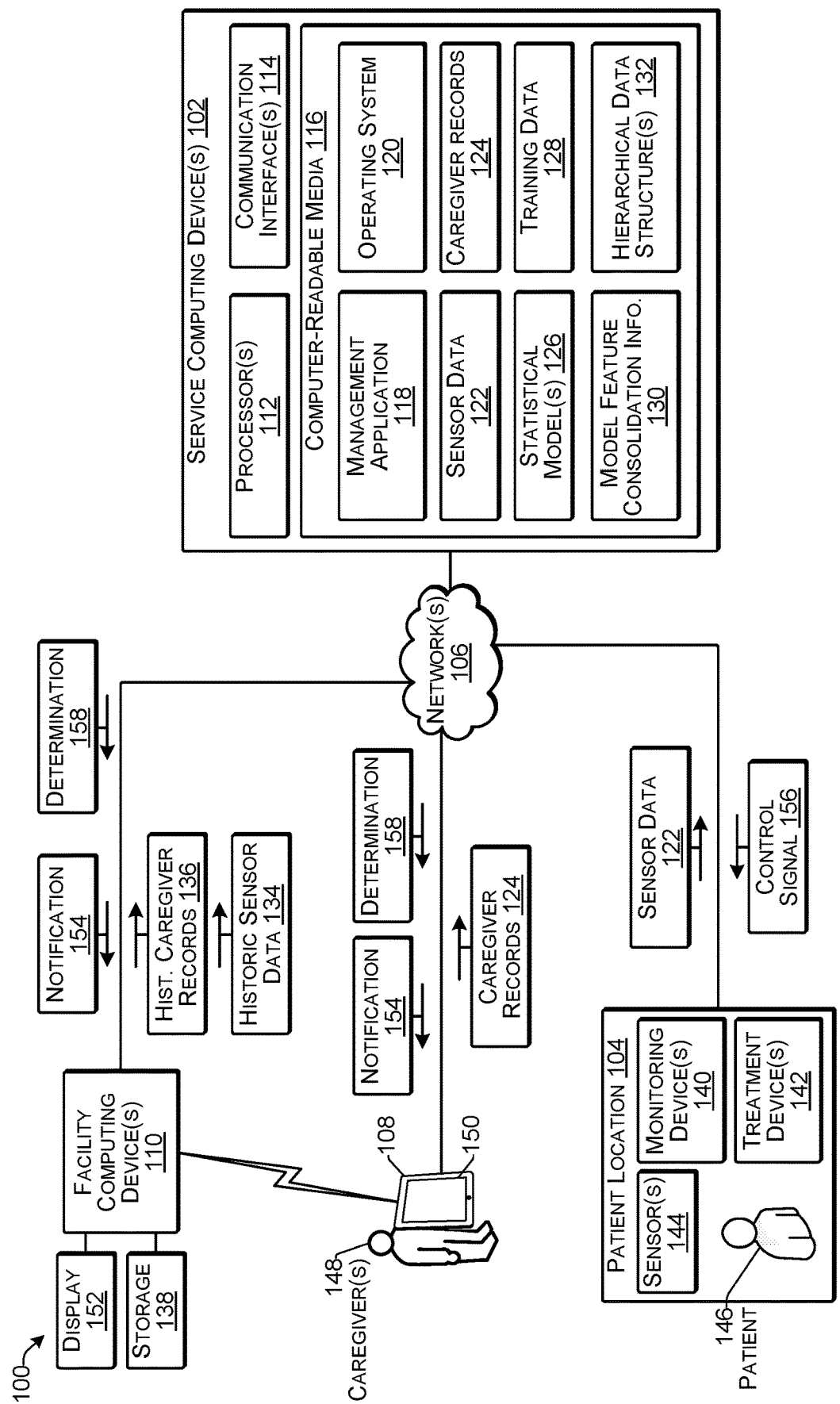
FIG. 1 illustrates an example architecture of a system able to control a device and/or provide a notification or other information as output according to some implementations.

Some implementations herein are directed to techniques and arrangements for considering large amounts of data for making determinations with respect to operation of treatment devices and/or for making determinations regarding patient care. As one example, sensor data from patient devices and information from caregiver records may be received as a large number of data inputs that a human would not be able to fully analyze. The data inputs may be used as features in a statistical model that provides an output that may be used by a management application for performing an action based on the output of the model, such as turning on or off a treatment device, changing a setting on a treatment device, sending an alert or other notification to a caregiver, making a determination about patient treatment effectiveness, making a determination about patient prognosis, making a determination regarding the likelihood of patient readmission, or the like.

Because the number of features for the statistical model (e.g., the number of distinct data inputs) may be very large (such as numbering in the hundreds, thousands, or more), implementations herein may attempt to combine or otherwise consolidate the features for the statistical model before training and using the statistical model for the above functions. For example, by reducing the number of features to be calculated for the statistical model without substantially affecting the results of the statistical model, implementations herein enable a computing device to execute the statistical model more quickly, thereby improving operation of the computing device performing the statistical model calculations. Additionally, in some examples, the feature consolidation techniques herein improve the operation of a medical device or other device that relies on the output of the statistical model for controlling its operation, such as by providing a faster determination of operating parameters and/or by enabling greater autonomous control of the medical device or other device.

Some examples herein employ machine learning to predict an outcome based on a large number of features. Further, at least some of these features may be organized into one or more data hierarchies. In addition, features at the same hierarchical level in the data hierarchy and under the same immediately higher-level node may be combined and consolidated into the immediately higher-level node in a manner that retains most of the original information for prediction while also respecting the hierarchical organization of the features. By rolling up or otherwise consolidating sets of multiple features into one feature per set, examples herein reduce the computational burden for the statistical modeling, both for training of the model and for executing the model to obtain an outcome. Further, having fewer features may enable more thorough exploration of the remaining features, such as in more complex models for a lower processing cost.

As one example, a service computing device, when determining whether to consolidate a subset of features in a set of features, may select an internal node n of maximum depth from among internal nodes not previously selected. If there are multiple such nodes, one of the internal nodes n not yet selected may be selected at random or based on other considerations. The features may correspond to the terminal nodes (also referred to as "leaf nodes") of a tree data structure that represents the data hierarchy. For the selected internal node n of maximum depth, the terminal nodes that are descendants of n correspond to "features under n". If the terminal nodes descending from the selected internal node n are able to be combined, the computing device may subsequently determine whether to keep the features separate under n or to roll up or otherwise consolidate these features. As discussed below, the computing device may determine whether consolidating the selected features will substantially affect the amount of information provided by the features. If the computing device determines that the consolidation will not substantially affect the information provided, the computing device may replace the subtree at n with a terminal node with the consolidated features. The computing device may determine whether to consolidate additional features based on a threshold level of predicted information loss.

Implementations herein may apply this technique to reduce the number of features in a data hierarchy so that a number of subtrees are converted into terminal nodes. The training dataset for the statistical model gains new features corresponding to those consolidated terminal nodes, and loses those features that were originally under those subtrees. As another example, if the original features are organized into multiple data hierarchies, then some implementations herein may apply the feature-reduction technique to each data hierarchy separately. Furthermore, while some examples herein use a tree data structure and associated terminology to describe the data hierarchy of the features, the examples herein are not limited to trees, and may encompass any type of data structure enabling a hierarchical expression of information.

To decide whether to replace the features under n with some aggregate function (e.g., sum, average, etc.) of the features, some examples may include evaluating the predicted absolute or relative loss of information for predicting a target variable "y". For instance, the predicted loss of information may be measured based on the value of a set of features for predicting y, such as based on a mutual information evaluation function, an R-squared evaluation function, or an inter-class/intra-class evaluation function. The consolidation of the features may be performed if the predicted loss of information is below a first threshold and if the total accumulated absolute loss of information does not exceed a second threshold. In addition, some examples may use different evaluation functions based on different information measures within the same application. The selection of an appropriate information measure depends on the characteristics of the target variable and characteristics of the features being considered for consolidation.

Rather than merely filtering out certain features, implementations herein consolidate features to construct new consolidated features while respecting the hierarchical organization of the original features within the hierarchical data. Further, if desired, additional feature consolidation may be performed in additional iterations after applying initial feature consolidation.

Some implementations may predict an outcome based on a plurality of features. There are many examples of datasets containing hierarchical features that may benefit from the techniques herein including clinical observations of patients in an ICU or other treatment facility; documents organized in a hierarchy by topic; search engine data on user visits to websites, and so forth. Further, some implementations provide a preprocessing stage before fitting a statistical model to predict a target variable. For instance, some examples selectively consolidate features in a hierarchy in a way that retains most of the original information for prediction while respecting the hierarchical structure. Thus, the techniques herein may be used to reduce the computational burden during training and use of a statistical model, and may enable the computing device executing the statistical model to execute more quickly and efficiently. Furthermore, medical devices or other devices that are controlled based on the output of the statistical model may be controlled more quickly and more accurately.

For discussion purposes, some example implementations are described in the environment of one or more computing devices that receive hierarchical data, such as sensor data and caregiver records, and apply the hierarchical data to a statistical model to provide an output, such as a notification sent to a caregiver computing device and/or a control signal sent for controlling a patient device. However, implementations herein are not limited to the particular examples provided, and may be extended to other types of data, other types of environments, other system architectures, other types of mathematical models, and so forth, as will be apparent to those of skill in the art in light of the disclosure herein. For instance, while some examples are described in the environment of providing medical care to a patient, implementations herein are not limited to this environment, and may be extended to other environments in which hierarchical data may be applied to a statistical model for determining an output useful for controlling a device, for providing a notification, for making a determination, or the like.

FIG. 1 illustrates an example architecture of a system 100 able to control a device and/or provide a notification or other information as output according to some implementations. The system 100 includes a least one service computing device 102 that is able to communicate with one or more patient locations 104, such as through one or more networks 106. Further, the service computing device 102 may be able to communicate through the one or more networks 106 with one or more caregiver computing devices 108 and one or more facility computing devices 110.

In some examples, the service computing device 102 may include one or more servers, personal computers, or other types of computing devices that may be embodied in any number of ways. For instance, in the case of a server, the modules, other functional components, and at least a portion of data storage may be implemented on at least one server, such as in a cluster of servers, a server farm or data center, a cloud-hosted computing service, and so forth, although other computer architectures may additionally or alternatively be used. In the illustrated example, the service computing device 102 includes, or may have associated therewith, one or more processors 112, one or more communication interfaces 114, and one or more computer-readable media 116.

Each processor 112 may be a single processing unit or a number of processing units, and may include single or multiple computing units, or multiple processing cores. The processor(s) 112 can be implemented as one or more central processing units, microprocessors, microcomputers, microcontrollers, digital signal processors, state machines, logic circuitries, and/or any devices that manipulate signals based on operational instructions. For instance, the processor(s) 112 may be one or more hardware processors and/or logic circuits of any suitable type specifically programmed or configured to execute the algorithms and processes described herein. The processor(s) 112 can be configured to fetch and execute computer-readable instructions stored in the computer-readable media 116, which can program the processor(s) 112 to perform the functions described herein.

The computer-readable media 116 may include volatile and nonvolatile memory and/or removable and non-removable media implemented in any type of technology for storage of information such as computer-readable instructions, data structures, program modules, or other data. For example, the computer-readable media 116 may include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the service computing device 102, the computer-readable media 116 may be a tangible non-transitory medium to the extent that, when mentioned, non-transitory computer-readable media exclude media such as energy, carrier signals, electromagnetic waves, and/or signals per se. In some cases, the computer-readable media 116 may be at the same location as the service computing device 102, while in other examples, the computer-readable media 116 may be partially remote from the service computing device 102.

The computer-readable media 116 may be used to store any number of functional components that are executable by the processor(s) 112. In many implementations, these functional components comprise instructions or programs that are executable by the processor(s) 112 and that, when executed, specifically program the processor(s) 112 to perform the actions attributed herein to the service computing device 102. Functional components stored in the computer-readable media 116 may include a management application 118 and an operating system (OS) 120. The management application 118 may include one or more computer programs, computer-readable instructions, executable code, or portions thereof that are executable to cause the processor(s) 112 to performing various tasks, such as for monitoring patient status, providing alerts, information, or other notifications to caregivers, and/or for controlling patient devices. Additionally, the operating system 120 may control and manage various functions of the service computing device 102. In some cases, the functional components may be stored in a storage portion of the computer-readable media 116, loaded into a local memory portion of the computer-readable media 116, and executed by the one or more processors 112. Numerous other software and/or hardware configurations will be apparent to those of skill in the art having the benefit of the disclosure herein.

In addition, the computer-readable media 116 may store data and data structures used for performing the functions and services described herein. For example, the computer-readable media 116 may store sensor data 122, caregiver records 124, one or more statistical models 126, training data 128, model feature consolidation information 130, and hierarchical data structures 132 that may be used by the management application 118. For example, the management application 118 may receive the sensor data 122 and the caregiver records 124 from one or more patients, may use this information in the one or more statistical models 126 to determine information about the respective patients.

As discussed additionally below, the management application 118 may use the one or more statistical models 126 to perform functions such as controlling patient devices, sending alerts or other notifications to caregivers, monitoring patient care, predicting patient outcomes, or the like. In some examples, the training data 128 may include historic sensor data 134 and historic caregiver records 136 for a plurality of past patients received from a storage 138 associated with the facility computing device(s) 110. The training data 128 may be received as hierarchical data and arranged as the hierarchical data structures 132. The management application may use the model feature consolidation information 130 to combine and consolidate the number of features in hierarchical data structures 132 to be used in the one or more the statistical models 126. The service computing device 102 may also include or maintain other functional components and data, which may include programs, drivers, etc., and other data used or generated by the functional components. Further, the service computing device 102 may include many other logical, programmatic, and physical components, of which those described above are merely examples that are related to the discussion herein.

The communication interface(s) 114 may include one or more interfaces and hardware components for enabling communication with various other devices, such as over the one or more networks 106. Thus, the communication interfaces 114 may include, or may couple to, one or more ports that provide connection to the network(s) 106 for communicating with the patient location(s) 104, the caregiver computing device(s) 108, and the facility computing device(s) 110. For example, the communication interface(s) 114 may enable communication through one or more of a LAN (local area network), WAN (wide area network), the Internet, cable networks, cellular networks, wireless networks (e.g., Wi-Fi) and wired networks (e.g., fiber optic, Ethernet, Fibre Channel), direct connections, as well as close-range communications such as BLUETOOTH®, and the like, as additionally enumerated elsewhere herein.

The patient location 104 may be a patient room or any other location where a patient may be treated. In some examples, each of the patient locations 104 may include a plurality of patient devices that may include one or more patient monitoring devices 140 and/or one or more patient treatment devices 142. Further, patient device sensors 144 may be associated with the monitoring device(s) 140 and/or the treatment device(s) 142, such as for detecting patient conditions and/or conditions of the monitoring devices 140 and/or the treatment devices 142. As one example, at least one patient 146 may be located at each of the patient locations 104, may be monitored by the monitoring device(s) 140, and may be treated by the treatment device(s) 142. Further, in some cases, a patient treatment device 142 may also be a patient monitoring device 140, and may include one or more of the sensors 144 for providing sensor data about the patient's condition.

In some examples, each of the patient devices 140, 142 may be able to communicate over the network 106 with the service computing device 102, such as to send sensor data 122 to the service computing device 102. In other examples, one of the patient devices 140, 142 may include a computing device that collects the sensor data 122 from other patient devices 140, 142 at the patient location 104, and that sends the sensor data 122 to the service computing device 102. As several examples, the patient monitoring devices 140 may include cardiac monitors, pulse oximeters, capnography monitors, respiratory rate monitors, neurological monitors, blood glucose monitors, fetal monitors, body temperature monitors, hemodynamic monitors, and/or various other types of monitoring devices. Further, the patient treatment devices 142 may include ventilators, intravenous (IV) infusion pumps, pacemakers, chest tubes, feeding tubes, anesthetic machines, heart-lung machines, dialysis machines, urinary catheters, defibrillators, and/or various other types of treatment devices.

The caregiver computing device(s) 108 and the facility computing device(s) 110 may be any suitable type of computing devices such as a desktop, workstation, server, laptop, tablet computing device, mobile device, smart phone, wearable device, or any other type of computing device able to send data over a network. In some cases, the caregiver computing device 108 and/or the facility computing device 110 may include hardware configurations similar to that described for the service computing device 102, but with different data and functional components to enable them to perform the various functions discussed herein. As one example, the caregiver computing device 108 may be a portable computing device, such as a tablet or laptop that a caregiver 148 carries when visiting patient locations 104, and the facility computing device 110 may be a server, workstation, desktop computer, e.g., located onsite at the care facility or at another location.

In some cases, the facility computing device 110 may be a server that stores patient records in the storage 138, which may include historic caregiver records 136 and historic sensor data 134 collected in the past for a plurality of patients 146, and which may be used as the training data 128 for the one or more statistical models 126. Further, in some examples, one or more of the facility computing devices 110 may be a monitoring computing device, such as at a central location in a care facility where the patient location 104 is located, e.g., at an ICU, or the like, to enable monitoring of individual patients at the care facility. The caregiver computing device 108 may include a display 150, and the facility computing device(s) 110 may include a display 152. Numerous other variations will be apparent to those of skill in the art having the benefit of the disclosure herein.

In some examples, the caregiver 148, such as a nurse, physician, physician's assistant, attendant, or other medical professional, may visit the patient(s) 146 at the patient location(s) 104, and may use the caregiver computing device 108 to enter or otherwise generate the caregiver records 124 for a particular patient 146. For instance, the caregiver records 124 may be related to the patient's condition, the settings or output of the patient monitoring devices 140, the settings or output of the patient treatment devices 142, caregiver observations, and so forth. In some examples, the caregiver records 124 may be entered in a structured manner as structured data, such as by enabling the caregiver 148 to make selections in a form, or the like. Alternatively, in other examples, the caregiver records 124 may be handwritten records, typed records, or otherwise free-form data that may be analyzed by the service computing device 102 or the facility computing device 110 following receipt thereby. The caregiver records 124 may be sent to the service computing device 102 by each caregiver computing device 108, such as when entered by the caregiver 148, when the caregiver 148 has finished seeing a particular patient 146, at the end of the caregiver's shift, or the like. Alternatively, the caregiver records 124 may be first sent to the facility computing device 110 and from there may be sent to the service computing device 102. Similarly, in some examples the facility computing device 110 may first receive the sensor data 122 and may forward the sensor data 122 to the service computing device 102.

The one or more networks 106 may include any type of network, including a local area network (LAN), such as an intranet; a wide area network (WAN), such as the Internet; a wireless network, such as a cellular network, a local wireless network, such as Wi-Fi, and/or short-range wireless communications, such as BLUETOOTH®; a wired network including fiber optics, Ethernet, Fibre Channel, or any other such network, a direct wired connection, or any combination thereof. Accordingly, the one or more networks 106 may include both wired and/or wireless communication technologies. Components used for such communications can depend at least in part upon the type of network, the environment selected, or both. Protocols for communicating over such networks are well known and will not be discussed herein in detail. Accordingly, the service computing device 102, the patient locations 104, the caregiver device(s) 108, and the facility computing device(s) 110 are able to communicate over the one or more networks 106 using wired or wireless connections, and combinations thereof.

In the example of FIG. 1, the management application 118 may be executed to receive the historic sensor data 134 and the historic caregiver records 136 as the training data 128. The statistical model(s) 126 may take into account numerous pieces of information obtained from the training data 128 that are referred to as features. According implementations herein, the features and other training data 128 may be arranged as hierarchical data, and the number of features may be consolidated, while maintaining the organization of the data hierarchy for use in the one or more statistical models 126. Following the reduction in the number of features according to the implementations herein, the statistical model may be trained using a revised hierarchical data structure having consolidated features, checked for accuracy, and then used for determining patient conditions, controlling patient devices, or the like. The statistical model(s) 126 may be periodically updated and re-trained based on new training data to keep the model(s) 126 up to date. Examples of suitable statistical models 126 that may be used in some implementations herein may include predictive models, decision trees, artificial neural networks, classifiers, regression models, such as linear regression models, support vector machines, and stochastic models, such as Markov models, hidden Markov models, and so forth.

After one or more statistical models 126 have been generated and trained, the sensor data 122 and the caregiver records 124 for a selected patient 146 may be used by the management application 118 as input to the one or more statistical models 126, such as to analyze the condition of the selected patient 146 and generate an output, such as for sending an alert or other notification 154 to at least one of the caregiver device 108 or the facility computing device(s)

110. For instance, the notification may be presented on the display 150 and/or 152 respectively, to notify the caregiver 148 or other medical personnel of a patient condition.

Additionally, or alternatively, the management application 118 may automatically adjust a setting of one or more patient devices 140, 142, such as by sending a control signal 156 for controlling a particular patient treatment device 142 or a particular patient monitoring device 140. For example, suppose that a treatment device 142 is an IV infusion pump, and the analysis performed using the statistical model 126 shows that the patient is receiving too much IV fluid. The control signal 156 may control the infusion pump to decrease the flow of IV fluid to the patient. As another example, the control signal 156 may control a monitoring device 140, such as to turn on a particular monitoring device 140 that may not have been on, but which may be used to further monitor the selected patient based on an indicated patient condition.

Furthermore, in some cases, one of the statistical models 126 may make a determination 158 about the patent 146, such as a diagnosis, a prognosis, a prediction of the efficacy of a long-term care treatment, a prediction as to whether the patient will have to be readmitted to the care facility if released, or the like. The management program 118 may send this determination to at least one of the caregiver computing device 108 or the facility computing device 110.

To prepare the one or more statistical models 126, implementations herein may determine the available features based on the historic sensor data 134 and the historic caregiver records 136. From this information, the management application 118 may generate one or more hierarchical data structures 132. The management application 118 may then attempt to reduce the overall number of features for a particular statistical model 126 (i.e., a particular target variable y) using model feature consolidation information 130. For example, the feature consolidation technique includes identifying features that may be rolled up or otherwise consolidated under an established data hierarchy while maintaining the hierarchy arrangement and without substantial loss of information that would affect the outcome provided by the statistical model 126. The details of reducing the number of features for a particular statistical model 126 are discussed additionally below.

FIG. 2 illustrates an example data structure 200 including hierarchical data according to some implementations. In this example, suppose that data is available regarding a number of observational units (e.g., past or current patients), and that this data may be used to configure and train a statistical model for predicting an outcome from a number of possible outcomes. As one example, in care facility such as the ICU of a hospital, it may be desirable to predict, for each patient who is currently on a ventilator, whether that patient is ready to be taken off the ventilator. Various sensors of patient devices may monitor the patients and provide sensor data. In addition, caregiver records may provide clinical observations about the patients, current ventilation scheduling, and other information about the patients. Both the sensor data and the caregiver records may provide potential predictors referred to herein as "features". For instance, it may be common to have a large number, e.g., hundreds, thousands, or more, features available for each patient. These features may be organized into one or more data hierarchies.

Data structure 200 is a table that includes a portion of example data including twelve descriptions used in clinical observations. For instance, in modern electronic health record systems, the number of descriptions may be in the thousands or more. Furthermore, these descriptions are typically organized in a hierarchy, which facilitates the data entry process using menus, submenus, sub-submenus, etc., and which makes it possible to summarize the data at different hierarchical levels of detail. Accordingly, in this example, a first level detail 202 includes "fluids in", "fluids out", "medications", "assessments", and so forth. A second level of detail 204 may include submenus of the first level 202. For example, "IV fluids" and "blood products" may be included in a submenu of "fluids in", "blood" and "urine" may be included in a submenu of "fluids out", "drugs" and "IV fluids" may be included in a submenu of "medications", and "conditions" may be included in a submenu of "assessments". In addition, a third level of detail 206 includes submenus of the second level 204. For example, "morphine" and "saline" may be included in a submenu of "IV fluids", "component 1" and "component 2" may be included in a submenu of "blood products", and "drug 1" and "drug 3" may be included in a submenu of "IV fluids". Furthermore, while three levels of detail are shown in this example, there may be many more levels of detail in some other examples. Accordingly, the management program 118 may receive, with the caregiver records, the descriptions used in the clinical observations, and may parse the information into the various hierarchical levels, as illustrated, to determine a hierarchical relationship for the received data. Received sensor data may similarly be arranged into a hierarchical relationship, such as based on a condition monitored, the type of sensor data, sensor data units, and so forth.

Figure 3:
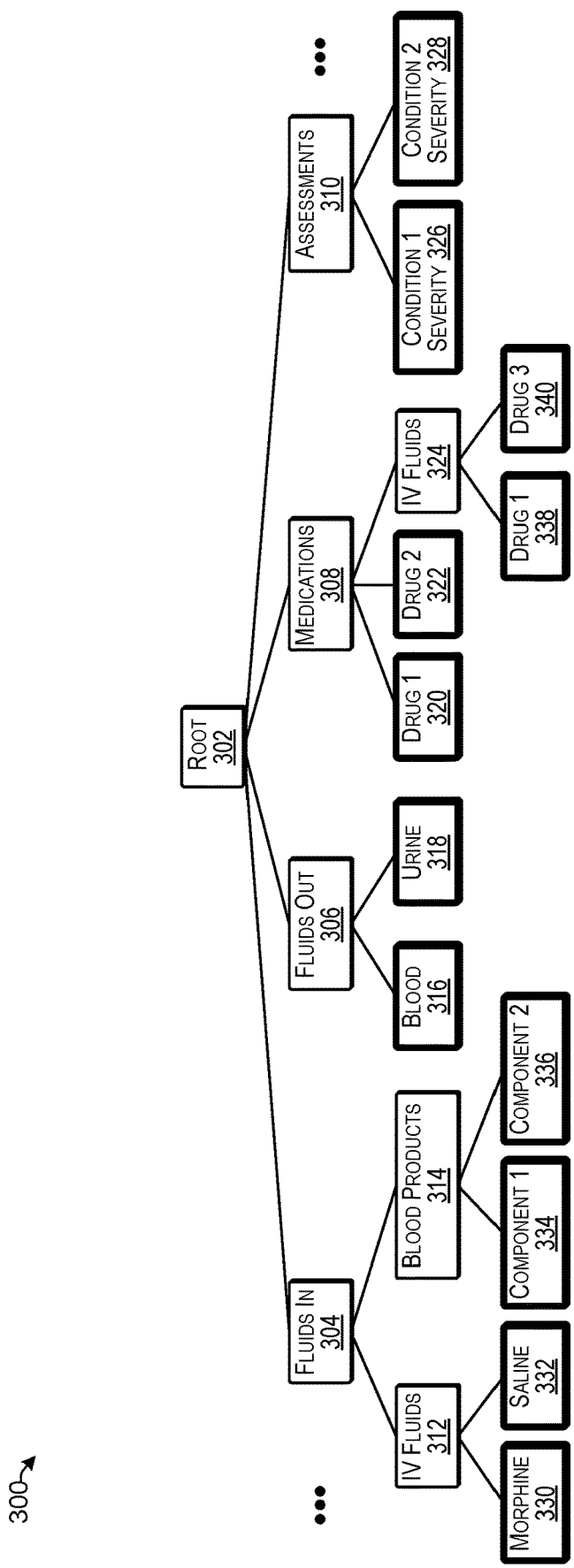
FIG. 3 illustrates an example of a tree data structure that is representative of a hierarchical data relationship according to some implementations.

FIG. 3 illustrates an example of a tree data structure 300 representative of a hierarchical data relationship according to some implementations. In this example, data from the table data structure 200 of FIG. 2 is represented as the tree data structure 300 including a plurality of nodes that represent the descriptions included in data structure 200 of FIG. 2. The tree data structure 300 includes a level zero node "root" 302 that sits atop the data hierarchy and that contains all the other nodes thereunder. The level one nodes include "fluids in" 304, "fluids out" 306, "medications" 308, and "assessments" 310. For instance, "fluids in" and "fluids out" may refer to fluids going into and out of the patient; "medications" may refer to medications used to treat the patient; and "assessments" may refer to various kinds of evaluations of the patient performed by the caregiver. Additionally, many more level one nodes may be included in some examples.

Furthermore, the level two nodes include, under fluids in 304, "IV fluids" 312 and "blood products" 314; under fluids out 306, "blood" 316 and "urine" 318; under medications 308, "drug 1" 320, "drug 2" 322, and "IV fluids" 324; and under assessments 310, "condition 1 severity" 326 and "condition 2 severity" 328. In addition, the level three nodes include, under IV fluids 312, "morphine" 330 and "saline" 332; under blood products 314, "component 1" 334 and "component 2" 336; and under IV fluids 324, "drug 1" 338 and "drug 3" 340. The tree 300 includes twelve terminal nodes 316, 318, 320, 322, 326, 328, 330, 332, 334, 336, 338, and 340, shown with a highlighted outline in FIG. 3, and each of which include an original description taken from the table data structure 200 of FIG. 2.

Each description of each terminal node may have some associated value, which may be a numerical measurement, a physical quantity, a categorical class (such as "on" or "off"; "1" or "0"; "true" or "false"; etc.), free text entered by a caregiver, and so forth. For the prediction problem in this example, a training dataset may be constructed from these values and a plurality of other data sources and based on the data hierarchy illustrated in FIG. 3. An example training dataset is discussed below with respect to FIG. 4.

FIG. 4 illustrates an example data structure 400 of a training data set for use by a statistical model according to some implementations. In this example, an observational unit 402 may be a particular patient-and-date combination that includes a patient ID 404 and a date 406. In addition, a target variable y 408 may be a target variable that is to be predicted by the statistical model. Further, the training data set 400 may include a plurality of features such as feature 1 410(1), feature 2 410(2), . . . , feature K 410(K) which correspond to the clinical observation descriptions of FIG. 2, or equivalently, to the terminal nodes of the tree data structure 300 of FIG. 3. In some cases, there may be hundreds or thousands of the features 410 in the training dataset 400.

The construction of such a training dataset 400 from raw data sources such as clinical observations typically may include aggregating the raw data values to the level of the observational unit. Given such a training dataset 400, and the feature hierarchy described above, implementations herein may consolidate multiple features 410 into a single feature. This enables the creation of a smaller training dataset having a smaller number of features. Some implementations herein may limit the consolidation of terminal nodes to consolidation with other terminal nodes under the same subtree, as this maintains the hierarchical structure. By reducing the number of features in the training dataset, the size of the statistical model is reduced and the amount of data managed each time the statistical model is executed is also reduced, thereby increasing the speed with which the statistical model may be executed and improving the operation of the computing device performing the calculations. This also improves the speed with which decisions can be made based on the statistical model, such as for sending an alert or other notification to a caregiver, and/or for sending a control signal for controlling a patient device, such as for turning on, turning off, or adjusting the patient device, thereby improving the operation of the patient device. Further, consolidating the features can enable the remaining features to be used more effectively in more complex models for similar processing costs.

FIGS. 5A-5B illustrate an example of the tree data structure 300 in which features are consolidated into a higher level node according to some implementations. In this example, the management application may examine the terminal nodes of the tree to see if any terminal nodes may be consolidated into the next higher level of the tree hierarchy. In FIG. 5A, the two features morphine, corresponding to terminal node 330, and saline, corresponding to terminal node 332, are considered for consolidation (i.e., rolling up) into the immediately higher level node, which is IV fluids 312. Thus, in this case, a subtree 502 includes nodes 312, 330 and 332. The morphine node 330 and the saline node 332 are both underneath the IV fluids intermediate node 312. Suppose that the terminal nodes 330 and 332 may both be expressed in milliliters. Accordingly, a consolidated feature represented by IV fluids node 312 may be expressed as a total volume of IV fluids provided to the patient. As another example, if the features of terminal nodes 330 and 332 are counts of the number of times that the particular fluids, morphine and saline, respectively, were administered, these counts may be combined by adding the counts together to obtain a total count of IV fluids administered as the feature represented by the IV fluids node 312.

In either case, or in the case of other units of measure or expression, a consideration for performing the consolidation is how much information is lost. In this example, instead of considering what volume of morphine the patient received and what volume of saline the patient received on a particular day, for purposes of some statistical models, it may be almost as informative to combine the two quantities as a total volume of IV fluids that were received by the patient on the particular day. On the other hand, for other statistical models, the amount of morphine and/or saline received by the patient may be an important consideration and therefore it may not be desirable to combine the two for consolidating the number of features. Accordingly, implementations herein determine whether combining particular features is acceptable for a particular statistical model, e.g., for determining a particular target variable y that is to be predicted by the statistical model.

As one example, given the training dataset 400 discussed above, and the feature hierarchy of the tree data structure 300, implementations herein may consider consolidating multiple features into one feature, thus obtaining a training set with a smaller number of features. Further, some implementations are limited to consolidating terminal nodes with other terminal nodes under the same subtree, as this maintains the hierarchical structure of the data. In addition, an aggregation function for combining multiple features into one feature at the next higher level may be provided by a user or other source for particular features, or alternatively may be determined from the context or category of the features to be consolidated.

In the illustrated example of FIG. 5A, the management application may determine a category of expression of the features. For instance, if the feature for the morphine node 330 and the feature for the saline node 332 may both be expressed as the same physical quantities, such as in units of volume, e.g., mL of IV fluid, the features may be consolidated by addition and expressed in terms of the total volume of IV fluids administered to the patient. On the other hand, if the feature for the morphine node 330 and the feature for the saline node 332 are both expressed in counts of the number of times that the respective fluids were administered, the features may be consolidated by addition of the total number of counts of IV fluids administered to the patient. Similarly, if the features for nodes 330 and 332 may be expressed as true or false indicators that the respective fluids were present, the consolidated feature may be an indicator that any kind of IV fluid was administered. Thus, in the foregoing cases, the terminal nodes 330 and 332 are compatible with each other and are therefore able to be consolidated if the amount of information lost from the consolidation is predicted to below a threshold and/or based on other considerations discussed below.

Other types of features may also be consolidated. For example, if "condition 1 severity" node 326 and "condition 2 severity" node 328 under the "assessments" node 310 are examined, they may or may not be combinable, depending on the form of the respective condition assessment. As one example, if the assessments of the condition 1 and condition 2 are measured on the same scale (e.g., 0 to 100), and are directionally consistent, e.g., larger values are better for both, the combined feature may be expressed as the average of the two values for the two assessments.

On the other hand, some features might not be able to be combined meaningfully. For instance, if the feature "IV fluids" at node 312 is expressed in total volume of liquid, and the "blood products" feature at node 314 indicates the number of times that "blood products" of any kind were administered, it may not make sense to combine the "IV fluids" feature at node 312 with the "blood products" feature at node 314. Thus, if the units or other categories of two features do not match, consolidation of the two features typically is not considered.

As illustrated in FIG. 5B, consolidating the "morphine" feature from node 330 and the "saline" feature from node 332 results in removal of nodes 330 and 332 from the data structure 300. Further, the IV fluids node 312 is now a terminal node and includes the feature "IV fluids" which, based on the aggregation function used, represents the consolidated IV fluids feature at node 312, such as the total volume of IV fluids delivered to the patient, or the like. Accordingly, through the consolidation of the features from nodes 330 and 332 into a new consolidated feature at node 312, the subtree 502 in FIG. 5A is replaced with what is now a terminal node 312 in FIG. 5B. A training dataset may be generated with the new consolidated feature, i.e., the "IV fluids" feature, that is used in place of the two original features at nodes 330 and 332 that correspond to the "morphine" and "saline" values, respectively.

Some implementations herein may determine whether to perform consolidation of certain features based on evaluation of the consolidated features. As one example, suppose that the current features are $x_1, x_2, \ldots, x_p$, (corresponding to the terminal nodes of a subtree). A consolidated feature u may be expressed as $u=f(x_1, x_2, \ldots, x_p)$, where $f$ is a given aggregation function. Several different techniques may be applied for ranking or otherwise evaluating the features in the context of predicting a given target variable y. Several examples of ranking functions that may be used for evaluating whether to perform a consolidation of selected features include:

(1) Mutual Information: determining mutual information between each $x_i$ and y, denoted as $I(y, x_i)$;
(2) R-Squared: determining a correlation coefficient between each $x_i$ and the target variable y, denoted as $r(y, x_i)$; or
(3) Inter-class/Intra-class Ratio: when the target variable y is a categorical variable, determining a ratio between an inter-class distance and an intra-class distance of each $x_i$.

The above evaluation functions (1)-(3) may be generalized to compare $\{x_1, x_2, \ldots, x_p\}$ as a set with $u=f(x_1, x_2, \ldots, x_p)$, and the comparison may be used to decide whether to consolidate selected features being considered for consolidation. This comparison technique may be performed using any ranking function that can be generalized to measure the value of a set of features to predict the target variable y.

It may be optimal to apply different evaluation functions in different cases depending at least partially on the nature of the features $x_1, x_2, \ldots, x_p$ being considered for consolidation and characteristics of the target variable y. In some examples, several different ranking functions may be used within the same hierarchy. As discussed below, the above ranking functions (1)-(3) may be generalized and used to determine whether to consolidate particular features. Additionally different ranking functions may be suitable for different types of features and/or for different target variables y.

(1) Mutual Information: As a first example, mutual information may be generalized for determining whether to perform a consolidation. Mutual information is a measure of the mutual dependence between the two variables. For instance, mutual information may quantify the amount of information (in units such as bits) obtained about one variable, through another variable. The concept of mutual information is linked to that of entropy of a random variable, which defines the "amount of randomness" held in a random variable.

For applying mutual information as an evaluation function, the set $\{x_1, x_2, \ldots, x_p\}$ is guaranteed to rank no worse than u, because $I(y; x_1, x_2, \ldots, x_p) \geq I(y; f(x_1, x_2, \ldots, x_p))$, where $f$ is the aggregation function. Accordingly, the difference $\Delta I$ between these mutual information values may be calculated where the difference $\Delta I$ represents the loss in information when consolidating $x_1, x_2, \ldots, x_p$ to u. As one example, the loss in information may be measured in "bits", which is a dimensionless quantity.

In some instances, the management application may determine to consolidate the features if the difference $\Delta I$ is less than a fixed, pre-specified threshold number of bits. As another example, the management application may determine to consolidate the features based on determining the relative loss of information, which may be determined based on: $\Delta I/I(y; x_1, x_2, \ldots, x_p)$, and which may provide a value between 0 and 1. For example, if the relative loss of information is less than a specified consolidation threshold b, such as 0.05, then the consolidation may be performed.

Determining mutual information may be employed when the target variable and the features are discrete, i.e., take on a small number of distinct values. One example of such an occurrence is when the target variable y is categorical and the features are true/false indicators of particular descriptions being present. When y or a feature is not discrete, binning may be used to calculate approximate mutual information. On the other hand, even when each feature has only two possible values, the combination of all p features can have $2^p$ possible values. When the number of features is large, the computation may be become slow or intractable.

(2) R-squared: As a second example, a correlation coefficient may be generalized as an evaluation function for determining whether to perform consolidation. For instance, the correlation coefficient may measure the degree of similarity between two rankings, and may be used to assess the significance of the relation between the two rankings. To generalize the correlation coefficient, some examples herein may use the coefficient of multiple correlation $R^2(y; x_1, x_2, \ldots, x_p)$, also known as "R-squared" in multiple linear regression. The value $1-R^2$ is the sum-of-squares of the residuals, denoted as $RSS(y; x_1, x_2, \ldots, x_p)$, when the target variable y is regressed on $x_1, x_2, \ldots, x_p$ relative to the sum-of-squares of y. The idea in this case is to calculate $\Delta RSS$, which is the difference between the residual sum-of-squares when the target variable y is regressed on $u=f(x_1, x_2, \ldots, x_p)$ and when the target variable y is regressed on $x_1, x_2, \ldots, x_p$. In general, there is no guarantee that the former will have at least as great a residual sum-of-squares as the latter (unlike in the mutual information example); however, this is true when u is a linear function of $x_1, x_2, \ldots, x_p$, which includes the common case in which $u=x_1+x_2+\ldots+x_p$.

In addition, even more generally, generalized linear models of y may be fitted on $x_1, x_2, \ldots, x_p$ and on u, and the difference in the deviances of the two models may be compared. One example of a generalized linear model is logistic regression, which is applicable when the target variable y is a categorical variable with two possible values. The notation $\Delta RSS$ may be extended to include this case. Thus, in some examples, the management application may determine to perform consolidation if $\Delta RSS$ is less than a specified threshold. In other examples, the management application may determine to perform consolidation if the relative change in residual sum-of-squares, $\Delta RSS/RSS(y;$ $x_1, x_2, \ldots, x_p$), is less than a specified consolidation threshold b, such as 0.05 or other specified consolidation threshold b. For linear regression, the relative change in the residual sum-of-squares is equal to the relative change in $1-R^2$.

Using the relative change in the residual sum-of-squares (including relative deviances) for determining whether to perform a consolidation may work well when the features are mostly continuous and linear regression models, or generalized linear models that are appropriate for fitting the target variable y. The R-squared evaluation function may typically be used when the target variable y is categorical with two possible results, e.g., true/false, 1/0, or the like. This technique may also scale well to a moderate number of features.

(3) Inter-class/Intra-class Ratio: As a third example, the ratio between inter-class distances and intra-class distances may be used as an evaluation function to determine whether to perform a consolidation. For instance, the inter-class/intra-class distance from individual features $x_i$ to the feature vector $(x_1, x_2, \ldots, x_p)$, may be generalized by using the Euclidean distance or another distance metric in the p-dimensional space. The change in the ratio of the inter-class/intra-class distances of $(x_1, x_2, \ldots, x_p)$ and of $u=f(x_1, x_2, \ldots, x_p)$ may then be compared. The decision as to whether to consolidate the selected features is then based on comparing the change or the relative change with a specified threshold.

To use inter-class/intra-class distance, the target variable y may be categorical. When the target variable y has more than two classes, standard logistic regression may not be applied, and hence it may not be possible to use the ΔRSS from logistic models. In such a case, implementations herein may apply the inter-class/intra-class distance. For example, there may be more than two classes and, thus, this evaluation technique may be used for implementations in which y has more than two discrete values. For many common distance metrics, the inter-class/intra-class distance computation scales well with the number of observations and the number of features.

After consolidating one or more sets of features, the management application may determine whether to stop or to consolidate additional sets of features. Several stopping criteria may be applied by the management application when determining whether to stop or keep going. As a first example, the management application may determine to stop when all internal nodes have been considered. This technique avoids endlessly repeating the same calculations and is the least stringent criterion. However, one disadvantage of this technique may arise because the decisions on whether to consolidate to the next higher node are made independently of decision for other intermediate nodes, such as based on meeting a threshold locally at each node. Using the mutual information as an example, the losses of mutual information ΔI, while individually may be small and below the threshold, may collectively result in an unacceptably large accumulated loss of information, which may hurt the prediction accuracy of the subsequent modeling.

One technique for mitigate this problem is to set a total-loss-of-information (TLI) threshold on the accumulated loss of mutual information, and stop the consolidation before this threshold is exceeded. This idea extends to ΔRSS, the change in inter-/intra-class distance, and other evaluation functions, as well as their relative counterparts such as $\Delta I/I(y; x_1, x_2, \ldots, x_p)$. If multiple evaluation functions are used, then a separate TLI threshold may be set for each evaluation function. Accordingly, in a case in which multiple evaluation functions are used for consolidating different features in the same data set, a first TLI threshold may be set for a first evaluation function, a second TLI threshold may be set for a second evaluation function, and so forth. When the first TLI threshold is reached for the first evaluation function, consolidation of features that have characteristics corresponding to the first evaluation function may be ceased, but consolidation of features that have characteristics corresponding to the second evaluation function may continue until the second TLI threshold has been reached, and so forth.

In some examples, the traversal of a set S of the multiple internal nodes of maximum depth (i.e., nodes 312, 314, 306, 324, and 310 in FIG. 5A) may be performed at random to determine whether to consolidate the terminal nodes of these nodes into the respective internal node. However, other techniques for traversing these internal nodes of maximum depth may be used to achieve better results in some cases. As one example, the set S of internal nodes of maximum depth may be traversed in an order that takes into account the comparative value and cost of each consolidation. For instance, if each consolidation is assigned the same value, one solution is to select the nodes in increasing order of cost, i.e., from the lowest cost to the higher costs until the TLI threshold is reached.

Alternatively, as another example, some implementations may include selecting for consolidation those features that combine a larger number of features, and may set the value based on the number of features being combined. However, this may lead to an optimization problem that is NP-hard. Accordingly, whether it is practical to solve this problem may depend at least partially on the number of nodes in S, which may be small enough for a brute force approach. Furthermore, while three examples of evaluation functions are described herein, other evaluation functions that may be used in addition to, or as an alternative to, these evaluation functions will be apparent to those of skill in the art having the benefit of the disclosure herein.

Figure 6:
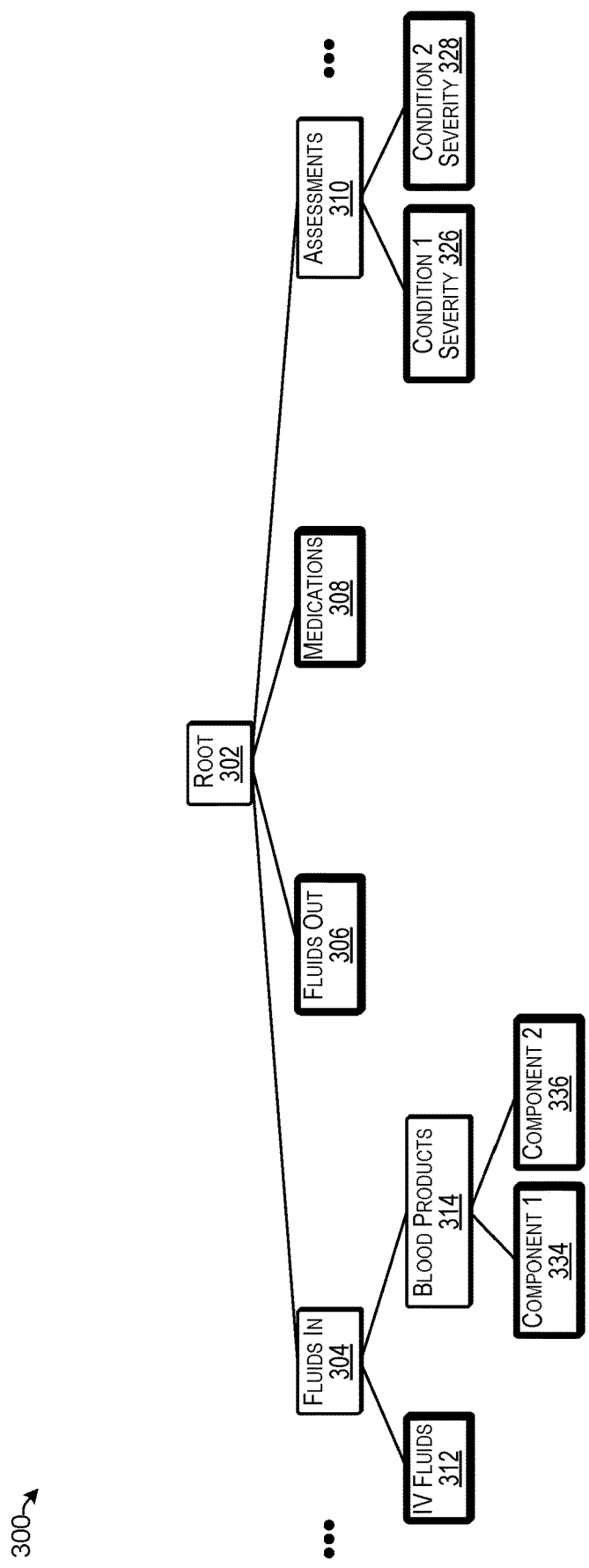
FIG. 6 illustrates an example of the tree data structure after finishing the consolidating of features according to some implementations.

FIG. 6 illustrates an example of the tree data structure 300 after finishing the consolidating of features according to some implementations. Suppose that after a number of consolidations of a plurality of feature sets the data hierarchy of the tree 300 becomes as shown in FIG. 6. In this example, the tree 300 now has seven terminal nodes, which is a substantial reduction from the original twelve terminal nodes. Accordingly, the statistical model fitted based on this data hierarchy will have five fewer features than if the feature consolidation processing had not been performed. As mentioned, this may reduce the processing time for training and using the statistical model, and therefore may improve the speed with which notifications are provided to caregivers and/or improve the speed and responsiveness for controlling devices, such as patient devices or the like.

In addition, consolidated features may be further consolidated, as indicated at 308. For example, referring back to FIG. 5B, suppose that initially, features at nodes 338 and 340 are consolidated into a new consolidated feature at node 324. Subsequently, such as during a second iteration of the process of FIG. 7, the new consolidated feature at 324 may be further consolidated with features 320 and 322 into a next higher hierarchical level by consolidation into a new further consolidated feature at node 308, as illustrated in FIG. 6.

Furthermore, implementations herein may be applied to other fields of endeavor. As one example, a dataset with such a hierarchical structure may also arise from machine learning methods, such as RuleFit, that derive additional features from the original ones using decision trees. In this case, the derived features may correspond to the nodes of the decision tree(s), and may represent "rules" defined in terms of the original features. Each rule may be a true/false indicator, and consolidating a set of rules may correspond to the logical "or" operator. The examples herein may also be used to selectively consolidate the derived features.

FIGS. 7-10 are flow diagrams illustrating example processes according to some implementations. The processes are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, frameworks and systems described in the examples herein, although the processes may be implemented in a wide variety of other environments, frameworks and systems.

Figure 7:
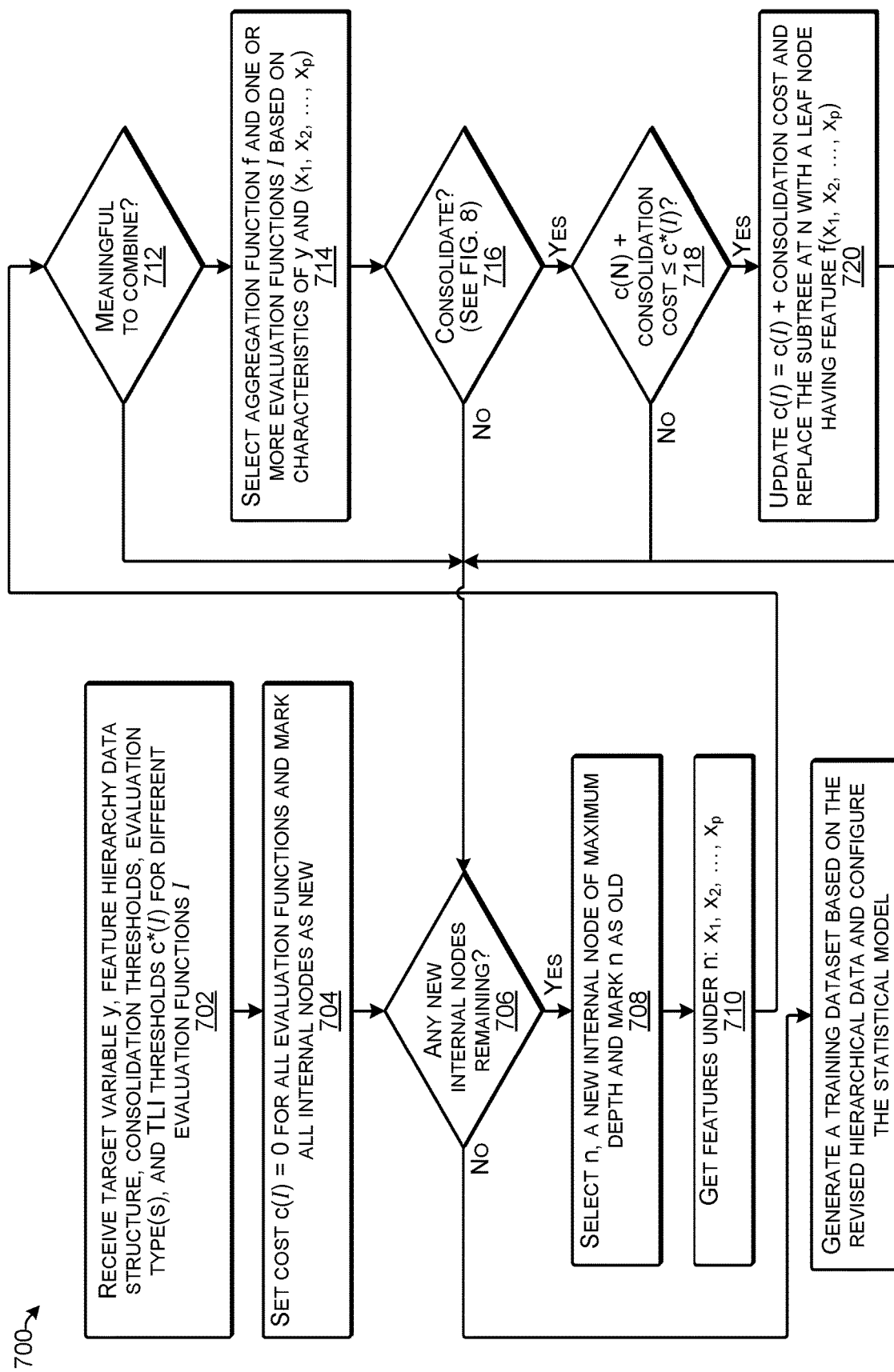
FIG. 7 is a flow diagram illustrating an example process for determining features to consolidate according to some implementations.

FIG. 7 is a flow diagram illustrating an example process 700 for determining features to consolidate according to some implementations. In some examples, the process 700 may be executed by the service computing device 102 or other suitable computing device.

At 702, the computing device may receive target variable y, feature hierarchy data structure, consolidation thresholds, evaluation function type(s), and TLI thresholds c*(I) for different evaluation functions I. For example, the characteristics of the target variable y may be known for the model being configured, e.g., discrete values, continuous values, etc. Further, based on the characteristics of the target variable y and the features, an evaluation function may be selected. For example, mutual information may be selected for cases in which the target variable y and the features are discrete, and the number of features is moderate; R-squared may be selected when the target variable y is categorical with two classes of values and the features are mostly continuous; and inter-class/intra-class ratio may be selected when the target variable is categorical and has more than two classes of values. Further, a TLI threshold may be selected based on the selected evaluation function, and may be selected based on a tradeoff between a desired level of accuracy for the model against processing speed for the model. As one non-limiting example, when the loss of information is measured as a relative value on a scale from 0 to 1, the TLI threshold may be between 0.10 to 0.20, or other desired TLI threshold. Each evaluation function may have its own TLI threshold, and thus, different evaluation functions may have different TLI thresholds. Further, the value of the TLI threshold may be specified at least partially based on whether an absolute difference is determined for the loss of information, or a relative difference is determined. The individual consolidation thresholds b may be set based on similar considerations.

At 704, the computing device may set the cost c(I)=0 for all evaluation functions and mark all internal nodes n of maximum depth as new.

At 706, the computing device may determine whether there are any new internal nodes n of maximum depth that have not yet been considered.

At 708, the computing device may select n, a new internal node of maximum depth and mark n as old.

At 710, the computing device may get features under n: $x_1, x_2, \ldots, x_p$. For example, p may be the number of features (number of terminal nodes) in the subtree having n as its root.

At 712, the computing device may determine whether it is meaningful to combine the features. For example, if the features are all of the same type, or otherwise have the same characteristics (e.g., can all be expressed as the same type of quantity; can all be expressed categorically, such as on/off, 0/1; and so forth) then the features are able to be combined and the process goes to 714. On the other hand if the features are not all of the same type (e.g., some features are expressed as a physical quantity, other features are expressed as a Boolean value, etc.) then it would not be meaningful to combine these features and the process goes to 706 to select another internal node n of maximum depth that has not yet been considered.

At 714, the computing device may select an aggregation function f and one or more evaluation functions I based on characteristics of y and $(x_1, x_2, \ldots, x_p)$.

Figure 8:
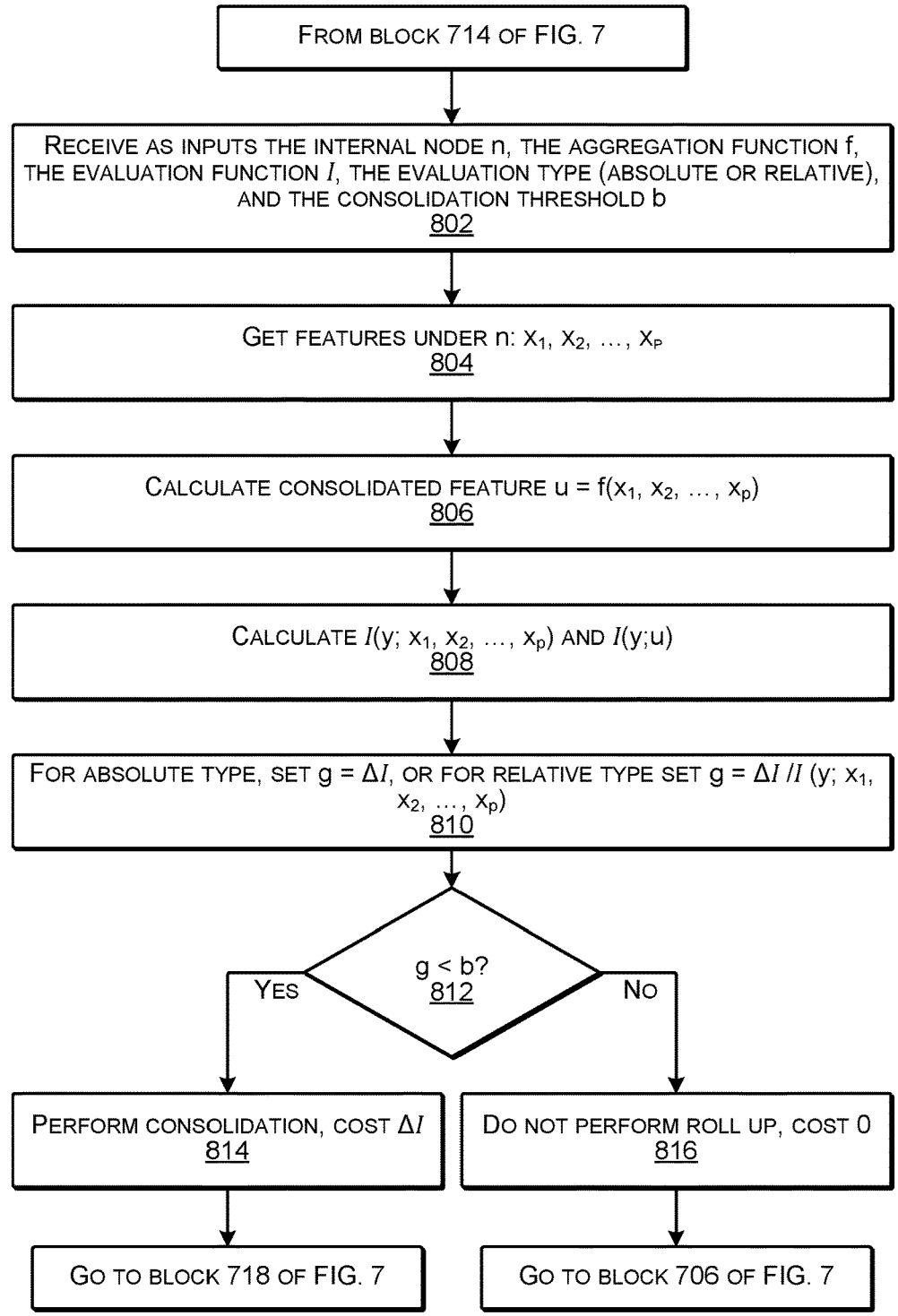
FIG. 8 is a flow diagram illustrating an example process that may be performed at block 716 of FIG. 7 for determining whether to consolidate selected features according to some implementations.

At 716, the computing device may determine whether to consolidate based on the selected evaluation function(s). If so, the process goes to 718; if not, the process goes back to 706 to determine if there are any other internal nodes remaining to be considered. FIG. 8 describes additional details of determining whether to consolidate particular features.

At 718, the computing device may determine whether the consolidation cost for consolidating the current feature plus the consolidation cost c(N) of any features already consolidated is cost ≤c*(I), the TLI threshold for the evaluation function. If so, the process goes to 720; if not, the process goes back to 706 to determine if there are any other internal nodes remaining to be considered. As mentioned above, in a case in which multiple evaluation functions are used for determining whether to consolidate different features in the same data set, a first TLI threshold may be set for the first evaluation function, a second TLI threshold may be set for the second evaluation function, and so forth. When the first TLI threshold is reached for the first evaluation function, consolidation of features that have characteristics corresponding to the first evaluation function may be ceased, but consolidation of features that have characteristics corresponding to the second evaluation function may continue until the second TLI threshold has been reached, and so forth.

At 720, the computing device may update the running total of the consolidation cost by adding the current consolidation cost, i.e., c(I)=c(I)+consolidation cost, and further, may replace the subtree at n with a terminal node having the new consolidated feature $f(x_1, x_2, \ldots, x_p)$. The process may then go back to 706 to determine if there are any other internal nodes remaining to be considered.

At 722, when all internal nodes have been considered, the computing device may generate a training dataset based on the revised hierarchical data and configure the statistical model. In some examples, the computing device may perform multiple iterations of blocks 702-720 before proceeding to block 722. For example, if the computing device completes a first iteration without exceeding the TLI threshold, the computing device may perform another iteration to determine if any of the consolidated features may be further consolidated to a next higher level in the hierarchical data structure. Thus, the process may be repeated until the TLI threshold would be exceeded, and block 722 may then be performed.

FIG. 8 is a flow diagram illustrating an example process 800 that is performed at block 716 of FIG. 7 for determining whether to consolidate selected features according to some implementations. In some examples, the process 800 may be executed by the service computing device 102 or other suitable computing device.

At 802, following block 714 of FIG. 7, the computing device may receive as inputs the internal node n, the aggregation function $f$, the evaluation function I, the evaluation type (absolute or relative), and the consolidation threshold b.

At 804, the computing device may get features under n: $x_1, x_2, \ldots, x_p$, which may be a subset of all the features in the hierarchical data. Accordingly, the selected subset of features $x_1, x_2, \ldots, x_p$ that depend from the selected internal node n are candidates for consolidation into the internal node n at the next higher hierarchical level in the structure of the hierarchical data.

At 806, the computing device may calculate consolidated feature $u=f(x_1, x_2, \ldots, x_p)$. For example, the aggregation function f is used to calculate the consolidated feature u. The aggregation function is selected based on the characteristics of the features $x_1, x_2, \ldots, x_p$.

At 808, the computing device may use the evaluation function to calculate a first result based on $I(y; x_1, x_2, \ldots, x_p)$ and to calculate a second result based on $I(y;u)$. For example, the selected evaluation function is used to calculate a first result based on no consolidation of $x_1, x_2, \ldots, x_p$, and to calculate a second result based on the consolidated feature u. A predicted loss of information for the consolidation may be determined based on the relative or absolute difference between the first result and the second result.

At 810, the computing device may, for determining an absolute difference, set $g=\Delta I$, or for determining a relative difference, set $g=\Delta I/I$ $(y; x_1, x_2, \ldots, x_p)$. For instance, the computing device may determine an absolute value of g as the difference between the first result and the second result determined at block 808. Additionally, or alternatively, the computing device may determine g as a relative value, in which the difference between the first result and the second result is divided by the first result. Accordingly, the value g may represent the predicted loss of information for the consolidation.

At 812, the computing device may determine whether the value g is less than the consolidation threshold b. The consolidation threshold b may be selected based on whether the absolute value for g is used or the relative value for g.

At 814, if g<b the computing device may perform the consolidation, and the cost of the consolidation is $\Delta I$. The process may then return to the process of FIG. 7 to continue processing at block 718 of FIG. 7.

At 816, on the other hand, if g>b, the computing device may determine not to perform the consolidation, and the cost is zero. The process may then return to the process of FIG. 7 to continue processing at block 706 of FIG. 7.

Figure 9:
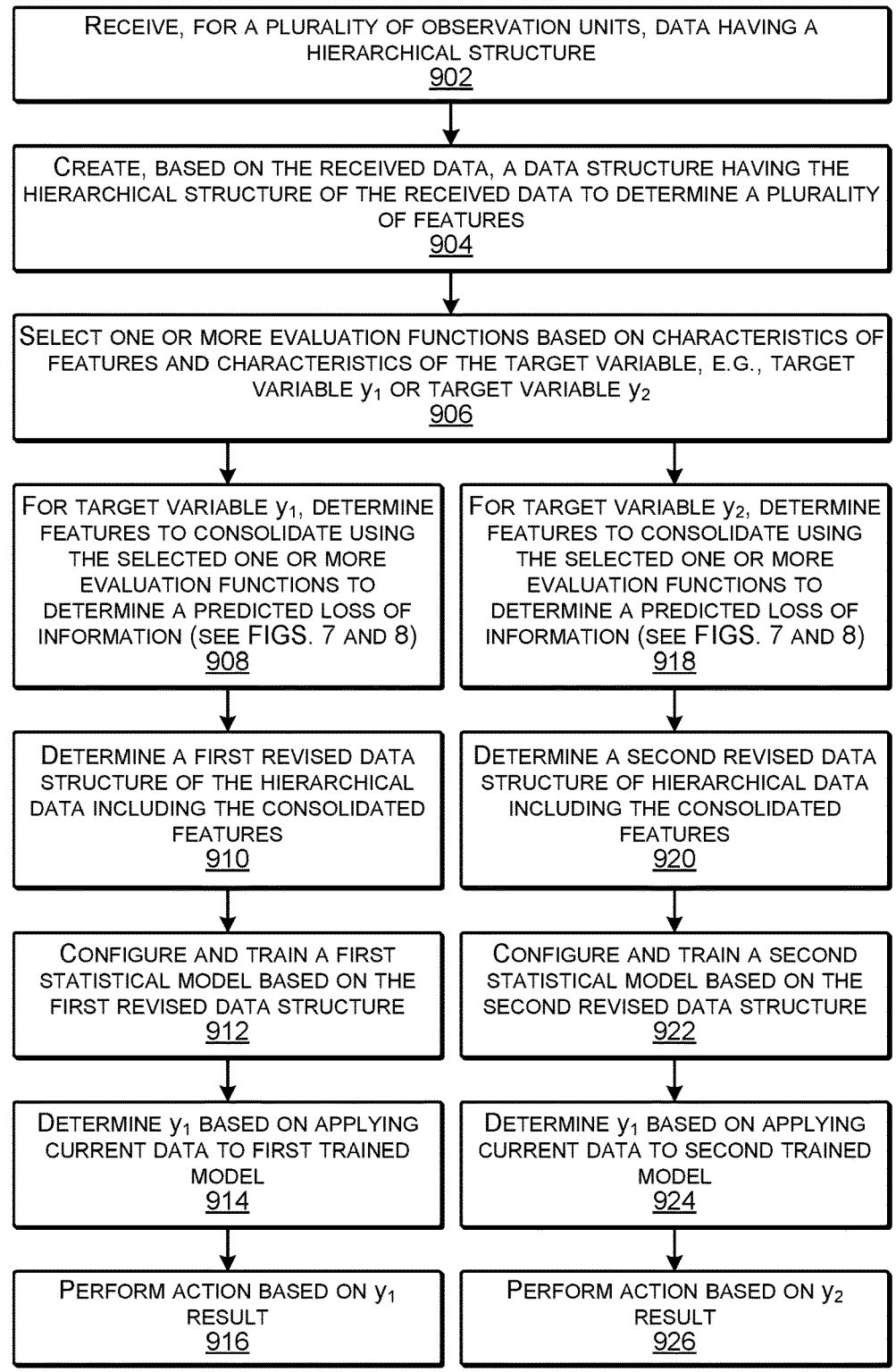
FIG. 9 is a flow diagram illustrating an example process including selecting evaluation functions according to some implementations.

FIG. 9 is a flow diagram illustrating an example process 900 including selecting evaluation functions according to some implementations. In some examples, the process 900 may be executed by the service computing device 102 or other suitable computing device.

At 902, the computing device may receive, for a plurality of observation units, hierarchical data having a hierarchical structure. In some examples, such as when used in a medical facility, the observation units may include patients, and the hierarchical data may include sensor data and/or caregiver records. However, in other examples, other types of data may be used for other types of statistical models in other types of applications.

At 904, the computing device may create, based on the received data, a data structure having the hierarchical structure of the received data to determine a plurality of features. For example, if the data structure is a tree, the plurality of features may correspond to the terminal nodes of the tree. If the data structure is a table indicating hierarchical levels, the plurality of features may correspond to farthest hierarchical level for each entry in the table. Further, while two example data structures are described herein, numerous other types of data structures that may be used for expressing the hierarchical data will be apparent to those of skill in the art having the benefit of the disclosure herein.

At 906, the computing device may select one or more evaluation functions based on characteristics of the features and characteristics of one or more target variables. For instance, suppose in this example there are two different target variables $y_1$ and $y_2$. As one example, suppose that $y_1$ is for a first statistical model that is used for predicting whether a ventilator is used, while $y_2$ is for a second statistical model that is used for predicting the length of stay of a particular patient in the care facility. Since the two different target variables may have different characteristics, different evaluation functions may be used for determining which features to consolidate in the hierarchical data for each of the two different target variables. For instance, in some examples multiple evaluation functions may be used for a single hierarchical dataset, depending on the nature of the features to be consolidated. As mentioned above, some evaluation functions are suitable for determining whether to consolidate some types of features and for some types of target variables, while other evaluation functions are suitable for determining whether to consolidate other types of features and for other types of target variables. Further, hierarchical data sets may include features having characteristics that differ from characteristics of other features in the same data set. Accordingly, in the example of FIG. 9, suppose that one or more evaluation functions are selected for determining the features to consolidate for determining the first target variable $y_1$, and one or more different evaluation functions are selected for determining which features to consolidate for determining the second target variable $y_2$. Alternatively of course, in other examples, the same one or more evaluation functions may be used in both cases if the target variables $y_1$ and $y_2$ have similar characteristics. Considerations that may be used for selecting evaluation functions are discussed above, e.g., with respect to FIGS. 5A and 5B.

At 908, for target variable $y_1$, the computing device may determine features to consolidate using the selected one or more evaluation functions. For example, the computing device may execute the processes of FIGS. 7 and 8 for determining which features to consolidate.

At 910, the computing device may determine a first revised data structure of the hierarchical data including the consolidated features.

At 912, the computing device may configure and train a first statistical model based on the first revised data structure.

At 914, the computing device may determine $y_1$ based on applying current data to first trained model.

At 916, the computing device may perform at least one action based on the $y_1$ result.

At 918, for target variable $y_2$, the computing device may determine features to consolidate using the selected one or more evaluation functions. For example, the computing device may execute the processes of FIGS. 7 and 8 for determining which features to consolidate.

At 920, the computing device may determine a second revised data structure of the hierarchical data including the consolidated features. In some examples, the consolidated features of the second revised data structure may be different from the consolidated features of the first revised data structure, such as based on different outcomes being determined from using different evaluation functions, e.g., based on different characteristics of the different target variables.

At 922, the computing device may configure and train a second statistical model based on the second revised data structure. In some examples, the second statistical model may be the same type of statistical model as the first statistical model, while in other examples, the second statistical model may be a different type of statistical model than the first statistical model. Examples of the types of statistical models that may be used according to some examples herein include predictive models, decision trees, artificial neural networks, classifiers, regression models, such as linear regression models, support vector machines, and stochastic models, such as Markov models, hidden Markov models, and so forth.

At 924, the computing device may determine $y_2$ based on applying current data to second trained model.

At 926, the computing device may perform at least one action based on the $y_2$ result.

Figure 10:
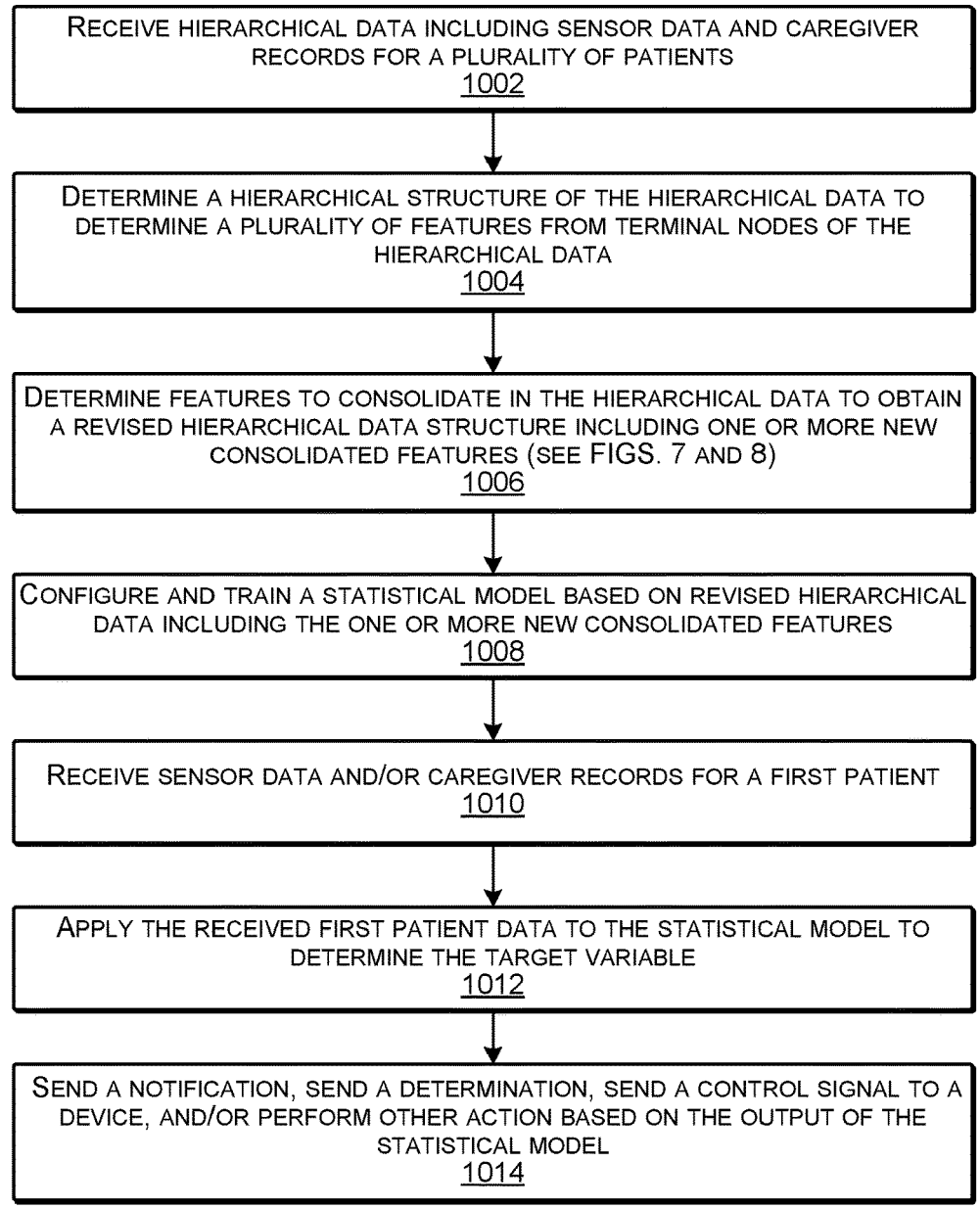
FIG. 10 is a flow diagram illustrating an example process for controlling a patient device and/or determining a patient condition according to some implementations.

FIG. 10 is a flow diagram illustrating an example process 1000 for controlling a patient device and/or determining a patient condition according to some implementations. In some examples, the process 1000 may be executed by the service computing device 102 or other suitable computing device. In this example, the techniques herein may be applied to patients and/or patient devices at a care facility, such as in the system corresponding to FIG. 1 discussed above.

At 1002, the computing device may receive hierarchical data including sensor data and caregiver records for a plurality of patients. The hierarchical data may have a hierarchical structure including a plurality of descriptions corresponding to different hierarchical levels in the hierarchical structure.

At 1004, the computing device may determine a hierarchical structure of the hierarchical data to determine a plurality of features. For example, the hierarchical data may be arranged in a data structure, such as a tree data structure, and the tree may include a plurality of terminal nodes that may correspond to features. Each of these features may be a candidate for consolidation with one of more other features in the same subtree.

At 1006, the computing device may determine features to consolidate in the hierarchical data to obtain revised hierarchical data including one or more new consolidated features. For example, the computing device may execute the processes of FIGS. 7 and 8 for determining features to consolidate in the hierarchical data to obtain a revised hierarchical data structure including one or more new consolidated features.

At 1008, the computing device may configure and train a statistical model based on the revised hierarchical data structure including the one or more new consolidated features.

At 1010, the computing device may receive sensor data and/or caregiver records for a first patient. For example, after the model has been trained, data for a particular patient may be applied to the model to determine a desired target variable for which the model has been configured.

At 1012, the computing device may apply the received first patient data to the statistical model to determine the target variable.

At 1014, the computing device may send a notification, send a determination, send a control signal to a device, and/or perform other action based on the output of the statistical model. As one example, the computing device may send a notification to a caregiver computing device and/or facility computing device. For instance, the computing device may send a notification to cause an alert to be presented on a display of the caregiver device and/or a display of the facility computing device. The notification may alert the caregiver to take corrective action and/or may perform other appropriate intervention.

As another example, the computing device may send a determination to another computing device. For instance, the determination may include a prediction regarding the first patient such as whether the first patient is likely to be readmitted in the near future to the care facility, the likelihood of the first patient requiring a particular treatment, or other desired information about the first patient.

Additionally, or alternatively, as another example, the computing device may send a signal to control a treatment device and/or a monitoring device. For instance, the computing device may send a control signal to control a treatment device at the patient location. In some cases, the computing device may turn on, turn off, or adjust a setting of a patient device, such as a treatment device or a monitoring device. A notification to a caregiver may also be sent in addition to sending the control signal to patient device. Further, in some examples, the control signal may only be sent to the patient device in certain situations, such as if a threshold level of urgency is determined.

The example processes described herein are only examples of processes provided for discussion purposes. Numerous other variations will be apparent to those of skill in the art in light of the disclosure herein. Further, while the disclosure herein sets forth several examples of suitable frameworks, architectures and environments for executing the processes, the implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Various instructions, processes, and techniques described herein may be considered in the general context of computer-executable instructions, such as program modules stored on computer-readable media, and executed by the processor(s) herein. Generally, program modules include routines, programs, objects, components, data structures, executable code, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed:

1. A system comprising:
one or more processors; and
one or more non-transitory computer-readable media maintaining executable instructions, which, when executed by the one or more processors, program the one or more processors to perform operations comprising:
receiving hierarchical data having a hierarchical structure including a plurality of hierarchical levels;
determining a plurality of features based at least in part on the hierarchical data;
selecting a subset of the features as candidates for consolidating to a next higher level in the hierarchical structure;
determining that a predicted loss of information from consolidating the subset of features plus a predicted loss of information for other consolidations of other features in the hierarchical data is less than a first threshold; and
revising the hierarchical structure to include a first consolidated feature rather than the subset of features.

2. The system as recited in claim 1, further comprising:
creating a statistical model based on the revised hierarchical structure including the first consolidated feature;
determining that a predicted loss of information from consolidating the subset of features is less than a second threshold by:
selecting an evaluation function based at least in part on a characteristic of a target variable of the statistical model;
calculating a first result of the evaluation function for the subset of features without consolidation and a second result of the evaluation function with consolidation of the subset of features; and
determining that a difference between the first result and the second result is less than the second threshold.

3. The system as recited in claim 2, wherein the determining that the predicted loss of information from consolidating the subset of features is less than a threshold comprises:
determining for the selected evaluation function the first threshold corresponding to a total loss of information;
determining the predicted loss of information for the consolidation at least partially based on the difference between the first result and the second result; and
determining that the predicted loss of information for the consolidation plus the predicted loss of information for the other consolidations of other features in the hierarchical data is less than the first threshold.

4. The system as recited in claim 2, the operations further comprising:
selecting a different evaluation function based at least in part on a characteristic of a different target variable of a different statistical model;
calculating a first result of the different evaluation function for the subset of features without consolidation and a second result of the different evaluation function with consolidation of the subset of features; and
determining that a difference between the first result of the different evaluation function and the second result of the different evaluation function is less than another consolidation threshold.

5. The system as recited in claim 4, the operations further comprising:
revising the hierarchical structure to generate another revised hierarchical structure including the first consolidated feature rather than the subset of features and at least one second consolidated feature;
training a different statistical model based on the other revised hierarchical structure;
receiving data to apply to the other statistical model; and
determining an output of the other statistical model.

6. The system as recited in claim 1, wherein the operation of receiving hierarchical data comprises receiving sensor data and caregiver records for a plurality of patients, wherein the sensor data is obtained from a plurality of patient devices and the caregiver records include data related to individual patients manually entered into a caregiver device, the operations further comprising:
training a statistical model based on the revised hierarchical structure including the first consolidated feature;
receiving sensor data and caregiver records corresponding to a first patient;
determining an output of the statistical model based on inputting at least a portion of at least one of the sensor data or the caregiver records; and
at least one of:
sending a notification or determination related to the first patient to a caregiver computing device; or
sending a control signal to a patient device associated with the first patient for controlling the patient device.

7. The system as recited in claim 1, the operations further comprising:
determining an aggregation function based on one or more common characteristics of the subset features;
using the aggregation function to determine the first consolidated feature by aggregating the subset of features using the aggregation function; and
determining the predicted loss of information based at least in part on a difference between the subset of features without aggregation and the first consolidated feature.

8. The system as recited in claim 1, the operations further comprising:
training a statistical model based on the revised hierarchical structure including the first consolidated feature;
receiving data to apply to the statistical model;
determining an output of the statistical model; and
sending at least one of:
a notification or determination to a computing device; or
a control signal to a device for controlling a device.

9. A method comprising:
receiving, by a processor, hierarchical data having a hierarchical structure;
determining a plurality of features based at least in part on the hierarchical data;
selecting a subset of the features as candidates for consolidating in the hierarchical structure;
determining an aggregation function based on one or more common characteristics of the subset of features;

using the aggregation function to determine the first consolidated feature by aggregating the subset of features using the aggregation function;

determining a predicted loss of information based at least in part on a difference between the subset of features without aggregation and the first consolidated feature;

determining that a predicted loss of information from consolidating the subset of features is less than a first threshold;

revising the hierarchical structure to include a first consolidated feature rather than the subset of features.

10. The method as recited in claim 9, further comprising:

training a statistical model based on the revised hierarchical structure including the first consolidated feature;

receiving data to apply to the statistical model;

determining an output of the statistical model; and sending a least one communication based on the output.

11. The method as recited in claim 9, wherein the determining that the predicted loss of information from consolidating the subset of features is less than a first threshold comprises:

selecting an evaluation function based at least in part on a characteristic of a target variable of the statistical model;

calculating a first result of the evaluation function for the subset of features without consolidation and a second result of the evaluation function with consolidation of the subset of features; and determining that a difference between the first result and the second result is less than the first threshold.

12. The method as recited in claim 11, further comprising:

determining for the selected evaluation function a second threshold corresponding to a total loss of information;

determining the predicted loss of information for the consolidation at least partially based on the difference between the first result and the second result; and determining that the predicted loss of information for the consolidation plus a predicted loss of information for other consolidations of other features in the hierarchical data is less than the second threshold.

13. The method as recited in claim 11, further comprising:

selecting a different evaluation function based at least in part on a characteristic of a different target variable of a different statistical model;

calculating a first result of the different evaluation function for the subset of features without consolidation and a second result of the different evaluation function with consolidation of the subset of features; and determining that a difference between the first result of the different evaluation function and the second result of the different evaluation function is less than another consolidation threshold.

14. The method as recited in claim 9, further comprising:

determining a predicted loss of information for consolidating the first consolidated feature with other features is less than the first threshold; and consolidating the first consolidated feature and the other features to a hierarchical level above a hierarchical level of the first consolidated feature.

15. A system comprising:

one or more processors; and one or more non-transitory computer-readable media maintaining executable instructions, which, when executed by the one or more processors, program the one or more processors to:

receive hierarchical data having a hierarchical structure with multiple hierarchical levels;

determine a plurality of features based at least in part on the hierarchical data;

select a subset of the features as candidates for consolidating to a next higher level in the hierarchical structure;

determine that a predicted loss of information from consolidating the subset of features is less than a threshold;

revise the hierarchical structure to include a first consolidated feature rather than the subset of features;

determine that a predicted loss of information for consolidating the first consolidated feature with other features is less than the first threshold; and consolidate the first consolidated feature and the other features to a higher hierarchical level above the hierarchical level of the first consolidated feature.

16. The system as recited in claim 15, wherein the one or more processors are further programmed to:

update the hierarchical structure to include the higher hierarchical level;

train a statistical model based on the updated hierarchical structure;

receive data to apply to the statistical model;

determine an output of the statistical model; and send a least one signal to control a device based on the output.

17. The system as recited in claim 15, wherein determining that the predicted loss of information from consolidating the subset of features is less than a first threshold comprises:

selecting an evaluation function based at least in part on a characteristic of a target variable of the statistical model;

calculating a first result of the evaluation function for the subset of features without consolidation and a second result of the evaluation function with consolidation of the subset of features; and determining that a difference between the first result and the second result is less than the first threshold.

18. The system as recited in claim 17, wherein the one or more processors are further programmed to:

determine for the selected evaluation function a second threshold corresponding to a total loss of information;

determine the predicted loss of information for the consolidation of the subset of features at least partially based on the difference between the first result and the second result; and determine that the predicted loss of information for the consolidation of the subset of features plus a predicted loss of information for other consolidations of other features in the hierarchical data is less than the second threshold.

19. The system as recited in claim 17, wherein the one or more processors are further programmed to:

determine an aggregation function at least partially based on one or more common characteristics of the subset of features;

use the aggregation function to determine the first consolidated feature by aggregating the subset of features using the aggregation function; and determine the predicted loss of information based at least in part on a difference between the subset of features without aggregation and the first consolidated feature.

* * * * *